United States Patent [19]

Tsushima et al.

[11] Patent Number: 5,550,260

[45] Date of Patent: Aug. 27, 1996

[54] PROCESS FOR THE PRODUCTION OF A CYCLOPENTENOL DERIVATIVE

[75] Inventors: Kazunori Tsushima, Sanda; Tomonori Iwasaki; Masaya Suzuki, both of Takarazuka; Noritada Matsuo, Itami, all of Japan

[73] Assignee: Sumitomo Chemical Company, Limited, Osaka, Japan

[21] Appl. No.: 253,065

[22] Filed: Jun. 2, 1994

[30] Foreign Application Priority Data

Jun. 3, 1993 [JP] Japan .................................. 5-133296

[51] Int. Cl.$^6$ ...................... C07C 35/06; C07D 307/02; C07F 7/08
[52] U.S. Cl. ...................... 549/421; 549/475; 556/465; 556/466; 556/489; 568/838
[58] Field of Search ...................... 568/838; 556/465, 556/466, 489; 549/421, 475

[56] References Cited

U.S. PATENT DOCUMENTS

| | | | |
|---|---|---|---|
| 4,304,733 | 12/1981 | Martel et al. | 560/122 |
| 4,356,187 | 10/1982 | Martel et al. | 424/304 |

FOREIGN PATENT DOCUMENTS

| | | |
|---|---|---|
| 55-147233 | 11/1980 | Japan . |
| 56-156238 | 12/1981 | Japan . |

OTHER PUBLICATIONS

*Bull. Chem. Soc. Jpn.,* vol. 53, No. 6, 1698–1702 (1980), K. Takai et al., "Wittig–type Reaction of Dimetallated Carbodianion Species as Produced by Zinc Reduction of *gem*–Polyhalogen Compounds in the Prsence of Lewis Acids".

*Tetrahedron Letters,* vol. 23, No. 41, pp. 4293–4296, 1982, L. Lombardo, "Methylenation of Carbonyl Compounds with $Zn-CH_2Br_2-TiCl_4$".

*Tetrahedron Letters,* vol. 25, No. 10, pp. 1067–1070, 1984, Y. Ogawa et al., "The Intramolecular Thermal ENE Reaction Route to (+)-9(0)-Methano-$\Delta^{6*9a)}$-$PGI_1$".

*J. Org. Chem.,* vol. 55, No. 13, pp. 4051–4063, 1990 (the left column on p. 4058, R. Jacobs et al.,"Defense Mechanisms of Arthropods. 84. Synthesis of (–)-a-Necrodol and (–)-β-Necrodol: Novel Cyclopentanoid Terpenese from a Carrion Beetle".

*J. Org. Chem.,* vol. 48, No. 13, pp. 2298–2300, 1983, L. Lombardo et al., "A New Strategy for $C_{20}$Gibberellin Synthesis: Total Synthesis of (±)-Gibberellin $A_{38}$MEthyl Ester".

*Tetrahedron Letters,* vol. 26, No. 45, pp. 5579–5580, 1985, J. Hibino et al., "Carbonyl Methylenation of Easily Enolizable Ketones".

*Org. Synth.,* 65, 81 (1987), pp. 81–89, L. Lombardo et al., "Methylenation of Carbonyl Compounds: (+)-3-Methylene-cis-p-Methane (Cyclohexane, 4-methyl-2-methylene-1-(1-methylethyl)-, R,R-)".

*Tetrahedron Letters,* No. 27, 1978, Oxford GB, pp. 2417–2420, K. Takeai et al.,"Effective Methods of Carbonyl Methylenation".

*Tetrahedron Letters,* No. 45, 1985, Oxford, GB, pp. 5581–5584, T. Okazoe et all,"Chemoselective Methylenation with a MEthylenedianion Synthon".

*Primary Examiner*—C. Warren Ivy
*Assistant Examiner*—Raymond Covington
*Attorney, Agent, or Firm*—Watson, Cole, Stevens Davis, P.L.L.C

[57] ABSTRACT

A process for the production of a cyclopentenol compound represented by the formula I:

$$R_1 \text{—cyclopentene with } CH_3, OH, CH_2 \text{ substituents} \quad (I)$$

wherein $R_1$ represents a 2-propenyl group or a 2-propynyl group from a cyclopentenolone compound represented by the formula II:

$$R_1 \text{—cyclopentene with } CH_3, OH, O \text{ substituents} \quad (II)$$

by protecting the hydroxyl group of the compound II, reacting the protected compound II with a reagent system obtained from $TiCl_4$, Zn and $CH_2Br_2$ or $CH_2I_2$ and removing the protecting group from the resulting reaction product.

10 Claims, No Drawings

PROCESS FOR THE PRODUCTION OF A CYCLOPENTENOL DERIVATIVE

FIELD OF THE INVENTION

The present invention relates to a process for producing a cyclopentenol derivative useful as an intermediate for the production of insecticides.

DESCRIPTION OF THE RELATED ART

A cyclopentenol compound represented by the formula I:

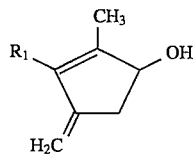

wherein $R_1$ represents a 2-propenyl group or a 2-propynyl group is disclosed as a useful intermediate for the production of insecticides in Japanese Patent Kokai 56-238 and 55-147233. However, the yield of said compound by the disclosed process was not satisfactory, which process comprised Wittig reaction of a cyclopentenolone compound II:

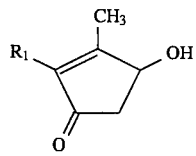

wherein $R_1$ is the same as defined above with a methyltriphenylphosphonium halide and a base. Hence an advantageous process which can provide said cyclopentenol compound I in good yields has been desired.

SUMMARY OF THE INVENTION

The inventors conducted a study to overcome the drawbacks of the above-mentioned method, and found out an advantageous process for producing said cyclopentenol compound I in good yields from the cyclopentenolone compound II using a protecting group and a reagent system comprising (a) titanium tetrachloride, (b) zinc and (c) dibromomethane or diiodomethane.

That is, one of the objects of the invention is to provide a process for the production of a cyclopentenol compound I:

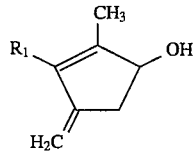

wherein $R_1$ represents a 2-propenyl group or a 2-propynyl group, which comprises the steps of;

(i) protecting the hydroxyl group of the cyclopentenolone compound II:

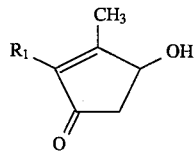

wherein $R_1$ is the same as defined above to give a cyclopentenolone derivative represented by the formula III:

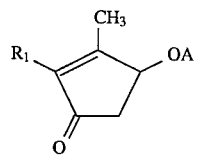

wherein $R_1$ is the same as defined above and A is a protecting group for a hydroxyl group;

(ii) reacting a mixture of zinc and dibromomethane or diiodomethane in an inert organic solvent with titanium tetrachloride;

(iii) reacting the resulting reaction mixture with the cyclopentenolone derivative III to give a cyclopentenol derivative IV:

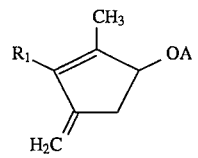

wherein $R_1$ and A are the same as defined above; and (iv) removing the protecting group A from the cyclopentenol derivative IV to give the cyclopentenol compound I.

Another object of the present invention is to provide a process for the production of a cyclopentenol derivative IV:

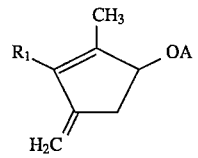

wherein $R_1$ and A are the same as defined above, which comprises the steps of;

(i) reacting a mixture of zinc and dibromomethane or diiodomethane in an inert organic solvent with titanium tetrachloride; and (ii) reacting the resulting reaction mixture with a cyclopentenolone derivative represented by the formula III:

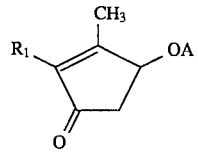

wherein $R_1$ and A are the same as defined above.

A further object of the present invention is to provide a cyclopentenol derivative IV:

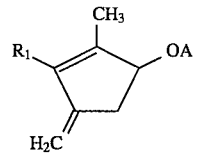

wherein $R_1$ and A are the same as defined above.

DESCRIPTION OF THE PREFERRED EMBODIMENTS

According to the present invention the cyclopentenol compound represented by the formula I that is useful for the production of the insecticides can be produced in good yields from the cyclopentenolone compound II.

The cyclopentenol compound represented by the formula I includes, for instance, following compounds:

(S)-2-methyl-4-methylidene-3-(2-propenyl)-cyclopent-2-ene-1-ol,
(S)-2-methyl-4-methylidene-3-(2-propynyl)-cyclopent-2-ene-1-ol,
(RS)-2-methyl-4-methylidene-3-(2-propenyl)-cyclopent-2-ene-1-ol, and
(RS)-2-methyl-4-methylidene-3-(2-propynyl)-cyclopent-2-ene-1-ol.

The first step of the process which provides the cyclopentenolone derivative III from the cyclopentenolone compound II will be explained next.

The protecting groups and procedures such as described on pp. 10~86 of Protective Groups in Organic Synthesis, 2nd Edition, T. W. Greene and P. G. M. Wuts, John Wiley & Sons, Inc. (1991) can be used for protecting the hydroxyl group of the cyclopentenolone compound II.

However, preferable examples of the protecting groups of the present invention are: a tri($C_1$–$C_6$)alkylsilyl group, a 2-tetrahydrofuranyl group, a 2-tetrahydropyranyl group and a ($C_1$–$C_2$)alkyl group substituted with a ($C_1$–$C_2$)alkoxy group at the α-position. The tri($C_1$–$C_6$)alkylsilyl group includes, for example, a trimethylsilyl group, a triethylsilyl group, a tert-butyldimethylsilyl group and a triisopropylsilyl group; and the ($C_1$–$C_2$)alkyl group substituted with a ($C_1$–$C_2$)alkoxy group at the α-position includes such a group as a methoxymethyl group, a 1-methoxyethyl group, an ethoxymethyl group or a 1-ethoxyethyl group.

As for the procedures, following i) ~iii) are preferably used in the present invention.

i) When A represents a tri($C_1$~$C_6$)alkylsilyl group, the cyclopentenolone compound II is usually reacted with a tri($C_1$~$C_6$)alkylsilylchloride or a tri($C_1$~$C_6$)alkylsilyltriflate in the presence of an organic base at the temperature of –30° C. ~50° C., preferably –10° C. ~20° C. in an aprotic organic solvent. The amount of the tri($C_1$~$C_6$)-alkylsilylchloride or the tri($C_1$~C6)alkylsilyltriflate is usually 1~2 moles, preferably 1~1.5 moles to the cyclopentenolone compound II. The amount of the base to be used is usually 1~10 moles, preferably 1.2~1.5 moles to the cyclopentenolone compound II. The organic bases to be used are: imidazole, triethylamine, diisopropylethylamine, pyridine, 2,6-dimethylpyridine or the like. The aprotic organic solvent to be used is a halogenated hydrocarbon solvent such as dichloromethane or the like, an ether solvent such as tetrahydrofuran or the like, an aprotic polar solvent such as dimethylformamide or the like, or a mixed solvent thereof.

ii) When A represents a 2-tetrahydrofuranyl group or a 2-tetrahydropyranyl group, the cyclopentenolone compound II is reacted with dihydropyran or dihydrofuran at the temperature of 0° C. ~ room temperature or 30° C. in the presence of a catalytic amount of an acid. The amount of dihydropyran or dihydrofuran to be used is usually 1~50 moles, preferably 1~10 moles to the cyclopentenolone compound II. The acid to be used in this reaction is, for example, an organic acid such as p-toluenesulfonic acid or the like, or an inorganic acid such as phosphoric acid, hydrochloric acid, sulfuric acid or the like, and a salt between such an acid as p-toluenesulfonic acid and such an organic base as pyridine. The reaction may be carried out in the presence of an aprotic organic solvent, examples of which include an ether solvent such as diethyl ether, tetrahydrofuran or the like, a hydrocarbon solvent such as benzene, toluene or the like, or a halogenated hydrocarbon solvent such as dichloromethane, chloroform or the like.

iii) When A represents a ($C_1$–$C_2$)alkyl group substituted with a ($C_1$–$C_2$)alkoxy group at the α-position, the cyclopentenolone compound II is usually reacted with a ($C_1$–$C_2$)alkyl chloride substituted with a ($C_1$–$C_2$)alkoxy group at the α-position at a temperature of –20° C.~50° C., preferably 0° C.20° C. in the presence of a base and an aprotic organic solvent. The amount of the ($C_1$–$C_2$)alkyl chloride substituted with a ($C_1$–$C_2$)alkoxy group at the α-position, to be used is usually 1~50 moles, preferably 1~5 moles to the cyclopentenolone compound II. The base to be used in this reaction is an organic base such as triethylamine, diisopropylethylamine, 2,6-dimethylpyridine or the like, or an alkali metal hydride such as sodium hydride, potassium hydride or the like. The amount of the base to be used is usually 1~10 equivalents, preferably 1~5 equivalents to the cyclopentenolone compound II. The aprotic organic solvent to be used is a halogenated solvent such as dichloromethane, chloroform or the like, an ether solvent such as diethyl ether, tetrahydrofuran or the like, or a hydrocarbon solvent such as benzene, toluene or the like.

Next, the step for producing the cyclopentenol derivative IV from the cyclopentenolone derivative III will be explained in detail.

The reaction of the cyclopentenolone derivative III with a reagent system comprising (a) titanium tetrachloride, (b) zinc and (c) dibromomethane or diiodomathane is usually conducted in the presence of an inert organic solvent, examples of which include a halogenated hydrocarbon solvent such as dichloromethane, chloroform or dichloroethane, an ether solvent such as tetrahydrofuran (THF) or diethyl ether, a hydrocarbon solvent such as toluene, or a mixed solvent thereof.

As for titanium tetrachloride, commercially available titanium tetrachloride (for example, a product sold by Kanto Chemical company) may be used as it is, or titanium tetrachloride which is diluted with an organic solvent such as dichloromethane or toluene may be used.

The amount of the titanium tetrachloride used is usually 0.5 to 5 moles, preferably 0.9 to 1.2 moles to the cyclopentenolone derivative III. Zinc is usually used in a powder form (zinc dust). As the powder form zinc, commercially available zinc (for example, zinc dust of up to 325 mesh, sold by Aldrich chemical company Inc.) may be used without any purification, or zinc may be used after being subjected to activation according to the method described on page 1276, vol. 1 (1967) of "Reagents for Organic Synthesis" edited by Fieser et al. The amount of the zinc used is usually 2 to 50 moles, preferably 4 to 10 moles to the cyclopentenolone derivative III.

The amount of dibromomethane or diiodomethane to be used is usually 1 to 10 moles, preferably 1 to 5 moles to titanium tetrachloride.

A typical example of the process comprises the steps of;
(i) reacting a mixture of zinc and dibromomethane or diiodomethane in an inert organic solvent with titanium tetrachloride; and (ii) reacting the resulting reaction mixture with a cyclopentenolone derivative represented by the formula III above to give the cyclopentenol derivative represented by the formula IV.

This reaction step is usually carried out by adding the titanium tetrachloride to a zinc suspended in an inert organic solvent containing dibromomethane or diiodomethane at −40° C.~50° C., preferably −20° C.~10° C., and the resulting reaction mixture is stirred at the same temperature, after which a cyclopentenolone derivative represented by the formula III is added thereto, while stirring maintaining the same temperature.

After completion of the reaction, for example, sodium bicarbonate and water are added to the reaction solution under ice-water cooling, and the resultant mixture is filtered. Then filtered solution is subjected to a post-treatment such as extraction with an organic solvent and/or concentration to isolate the desired product, or a solution of the desired product obtained after the post-treatment may be used in the following reaction as it is. The isolated product can be further purified, if necessary, by such an operation as column chromatography or distillation.

When an optically active cyclopentenolone derivative represented by the formula III, which is obtained from an optically active cyclopentenolone compound II without racemization in the previous step, is used, an optically active cyclopentenol derivative represented by the formula IV can be obtained with retention of the configuration, hence the present invention includes both racemic mixtures and optically active isomers of the compounds represented by the formulae III and IV.

The cyclopentenol derivative represented by the formula IV includes, for instance, following compounds:

(S)-2-methyl-4-methylidene-3-(2-propenyl)-1-trimethylsilyloxy- 2-cyclopentene,
(S)-2-methyl-4-methylidene-3-(2-propynyl)-1-trimethylsilyloxy- 2-cyclopentene,
(S)-2-methyl-4-methylidene-3-(2-propynyl)-1-tert-butyldimethylsilyloxy- 2-cyclopentene,
(S)-2-methyl-4-methylidene-3-(2-propynyl)-1-triethylsilyloxy- 2-cyclopentene,
(S)-2-methyl-4-methylidene-3-(2-propynyl)-1-triisopropylsilyloxy- 2-cyclopentene,
(S)-2-methyl-4-methylidene-3-(2-propenyl)-1-tert-butyldimethylsilyloxy- 2-cyclopentene,
(RS)-2-methyl-4-methylidene-3-(2-propenyl)-1-triethylsilyloxy- 2-cyclopentene,
(RS)-2-methyl-4-methylidene-3-(2-propynyl)-1-trimethylsilyloxy- 2-cyclopentene,
(S)-2-methyl-4-methylidene-3-(2-propynyl)-1-(2-tetrahydropyranyl)oxy-2-cyclopentene,
(S)-2-methyl-4-methylidene-3-(2-propynyl)-1-methoxymethyloxy- 2-cyclopentene,
(S)-2-methyl-4-methylidene-3-(2-propenyl)-1-(2-tetrahydropyranyl)oxy-2-cyclopentene,
(RS)-2-methyl-4-methylidene-3-(2-propynyl)-1-methoxymethyloxy- 2-cyclopentene, and
(S)-2-methyl-4-methylidene-3-(2-propynyl)-1-ethoxyethyloxy- 2-cyclopentene.

Next, the removal of the protecting group A is conducted according to the procedures such as described on pp. 10~86 of Protective Groups in Organic Synthesis, 2nd Edition, T. W. Greene and P. G. M. Wuts, John Wiley & Sons, Inc. (1991).

However, the procedures of i)~iii) described below are preferably employed to remove the protecting group A.

i) When A represents a tri($C_1$~$C_6$)alkylsilyl group, the cyclopentenol derivative having said protecting group A is reacted with a fluoride ion such as tetrabutylammonium fluoride or hydrofluoric acid(hydrogen fluoride), or an acid which includes a mineral acid such as hydrochloric acid or sulfuric acid, or an organic acid such as formic acid or acetic acid, and the reaction is usually conducted at the temperature of 0° C.~30° C. in an ether solvent such as tetrahydrofuran, diethyl ether or the like, a halogenated hydrocarbon solvent such as dichloromethane or the like, a hydrocarbon solvent such as benzene, toluene or the like, or a protic solvent such as water, methanol, ethanol or the like. When A is a trimethylsilyl group, the group may be removed by contacting the silylated compound with water.

ii) When A represents a 2-tetrahydrofuranyl group or a 2-tetrahydropyranyl group, the cyclopentenol derivatives having said protecting group A is reacted with a catalytic to excess amount of an acid (an organic acid such as p-toluenesulfonic acid or its salt, or a mineral acid such as hydrochloric acid or sulfuric acid), and the reaction is usually conducted in a protic solvent such as water, methanol or ethanol, an aprotic organic solvent such as an ether solvent (e.g. diethyl ether, tetrahydrofuran or the like), or a mixed solvent thereof at 0° C.~50° C.

iii) When A represents a ($C_1$–$C_2$)alkyl group substituted with a ($C_1$–$C_2$)alkoxy group at the α-position, the cyclopentenol derivative having said protecting group A is reacted with an acid. An example of the acid is an organic acid such as formic acid, acetic acid or methanesulfonic acid, or a mineral acid such as hydrochloric acid or sulfuric acid. The reaction is usually carried out in an ether solvent such as diethyl ether, tetrahydrofuran or the like, a protic solvent such as water, methanol, ethanol or the like, or a mixed solvent thereof at 20° C. to the refluxing temperature of the solvent.

The cyclopentenol compound I is obtained by a usual post-treatment after the procedures of i)~iii) above.

According to the above-described procedures, cyclopentenol compound represented by the formula I which is an intermediate of insecticides disclosed in Japanese Patent Kokai 56-156238 and 55-147233 can be obtained in good yields from the cyclopentenol derivative IV. The present process provides the cyclopentenol compound I in good yields from the cyclopentenolone compound II with retention of the configuration.

The cyclopentenolone compounds represented by the formula II above, the starting material of the present invention includes those compounds such as (RS)4-hydroxy-3-methyl-2-(2-propynyl)cyclopent-2-ene-1-one and (RS)-4-hydroxy-3-methyl-2-(2-propenyl)cyclopent-2-ene- 1-one, which can be produced by such a method as described in Agric. Biol. Chem., 46 (7), 1911~1912 (1982). An optically active cyclopentenolone compound II such as (S)-4-hydroxy-3-methyl-2-(2-propynyl)cyclopent2-ene-1-one can be produced, for example, by the method describe in Pestic. Sci., 11, 202 (1980) or Tetrahedron Letters, 32 (38), 5119~5122 (1991).

Production examples will further illustrate the present invention as follows, however it is not construed to limit the scope of the invention thereto.

EXAMPLE 1

① (S)-4-hydroxy-3-methyl-2-(2-propynyl)-cyclopent-2-ene-1-one (50.0 g) was dissolved in dry dimethylformamide (600 ml), and imidazole (27.3 g) was added to the dimethylformamide solution. Tert-butyldimethylchlorosilane (55.3 g) was added to the solution under ice-water cooling and the resulting mixture was allowed to react for 2 hours, then for 13 hours at 20° C. The reaction solution was poured into an aqueous oxalic acid solution under ice-water cooling, and extracted three times with diethyl ether (200 ml). The ether layers were combined, and the combined layer was washed with saturated aqueous sodium bicarbonate solution and brine in sequence. After dried over anhydrous sodium sulfate, the solvent was evaporated under reduced pressure. The resultant residue was subjected to distillation under reduced pressure to afford (S)-4-tert-butyldimethylsilyloxy-3-methyl-2-( 2-propynyl)cyclopent-2-ene-1-one (76.0 g, yield 86.0%) as a pale yellow oil.

b.p. 136°~139° C. (4 mmHg)

$[\alpha]_D^{23}$+30.5° (neat)

$^1$H-NMR (solvent: CDCl$_3$, internal standard: TMS) δ value (ppm): 4.69(brd, 1H), 3.11(ABq, 2H), 2.74(dd, 1H), 2.28(dd, 1H), 2.16(s, 3H), 1.96(t, 1H), 0.92(s, 9H), 0.15(s, 3H), 0.12(s, 3H). ② Dibromomethane (13.04 g) and zinc dust (14.71 g) were added to tetrahydrofuran (120ml), and the resulting mixture was cooled to 0°~5° C. A dichloromethane solution (50 ml) of 1M titanium tetrachloride was added to the tetrahydrofuran solution over about 10 min, and the resulting mixture was allowed to react for 3 days at 0°~5° C. Then a solution of (S)-4-tert-butyldimethylsilyloxy-3-methyl-2-(2-propynyl)cyclopent- 2-ene-1-one (13.22 g) in dichloromethane (50 ml) was added at 0°~5° C. over about 10 min. After the reaction was continued for 2 hours at the same temperature, hexane (200 ml) and then a slurry consisting of sodium bicarbonate (75 g) and water (40 ml) were added After stirring for 2 hours at 0°~5° C., the organic layer was separated by decantation. The obtained residue was extracted three times with n-hexane (200 ml). The combined organic layer was washed with saturated aqueous sodium bicarbonate solution, and dried over anhydrous sodium sulfate. The solvent was evaporated under reduced pressure, and the resultant residue was subjected to silica gel column chromatography (eluent; n-hexane: ethyl acetate=50:1) to afford the desired product, (S)-2-methyl-4-methylidene-3-(2-propynyl)- 1-tert-butyldimethylsilyloxy-cyclopent-2-ene (9.02 g, yield 68.7%) as a pale yellow oil.

$[\alpha]_D^{19}$−74.5° (c=3.07, CHCl$_3$)

$^1$H-NMR (solvent: CDCl$_3$, internal standard: TMS) δ value (ppm): 4.91(s, 1H), 4.77(s, 1H), 4.66(br, 1H), 3.08(br, 2H), 2.90(dd, 1H), 2.38(m, 1H), 1.95(t, 1H), 1.83(s, 3H), 0.92(s, 9H), 0.11(s, 3H), 0.09(s, 3H).

③ To a solution of (S)-2-methyl-4-methylidene- 3-(2-propynyl)-1-tert-butyldimethylsilyl-oxycyclopent- 2-ene (7.52 g, obtained above) in tetrahydrofuran (50 ml) was added a solution mixture (30 ml) consisting of tetrahydrofurane solution (80 parts) of 1M tetrabutylammonium fluoride and 46% hydrogenfluoride (3 parts) under ice-water cooling. The solution was then stirred at room temperature for 14 hours. The reaction solution was poured into ice-water, and then extracted with ether (150 ml ×2). The ether layers were combined, and washed with brine, and dried over anhydrous sodium sulfate. The solvent was evaporated under reduced pressure. The resultant residue was subjected to silica gel column chromatography (eluent; n-hexane: ethyl acetate=2:1) to afford the desired product (S)-2-methyl- 4-methylidene-3-(2-propynyl)cyclopent-2-ene-1-ol (3.40 g, yield 81.0%) as a pale yellow oil.

$^1$H-NMR (solvent: CDCl$_3$, internal standard: TMS) δ value (ppm): 4.97(s, 1H), 4.84(s, 1H), 4.64(br, t, 1H), 3.10(d, 2H), 2.99(m, 1H), 2.38(m, 1H), 1.96(t, 1H), 1.92(s, 3H), 1.48(d, 1H).

$[\alpha]_D^{23}$−116.1° (C=2.43, CHCl$_3$) m.p. 73.2° C.

EXAMPLE 2

① (RS)-4-hydroxy-3-methyl-2-(2-propenyl)-cyclopent-2-ene-1-one (5.0 g) and imidazole (2.91 g) were dissolved in dry dimethylformamide (20 ml), and tert-butyldimethylchlorosilane (5.45 g) was added thereto at room temperature and the resulting mixture was allowed to react for 14 hours at room temperature. The reaction solution was poured into an ice-cooled aqueous citric acid solution, and extracted three times with diethyl ether. The organic layers were combined, and the combined layer was washed with saturated aqueous sodium bicarbonate solution and brine in sequence, and dried over anhydrous sodium sulfate. The solvent was evaporated under reduced pressure. The resultant residue was subjected to column chromatography (eluent; n-hexane: ethy acetate=4:1) to afford (RS)-4-tert-butyldimethylsilyloxy- 3-methyl-2-(2-propenyl)cyclopent-2-ene-1-one (8.48 g, yield 97.0%) as a pale yellow oil.

$^1$H-NMR (solvent: CDCl$^3$, internal standard: TMS) δ value (ppm): 5.77(m, 1H), 5.00(m, 2H), 4.67(m, 1H), 2.95(m, 2H), 2.71(dd, 1H), 2.24(dd, 1H), 2.03(s. 3H), 0.92(s, 9H), 0.15(s, 3H), 0.12(s, 3H).

② Dibromomethane (6.13 g) and zinc dust (6.92 g) were added to dry tetrahydrofuran (100 ml), and the resulting mixture was cooled to 0°~5° C. A dichloromethane solution (25.9 ml) of 1M titanium tetrachloride was added to the tetrahydrofuran solution in about 10 min, and the resulting mixture was allowed to react for 4 days at 0°~5° C. Then a solution of (RS)-4-tert-butyldimethylsilyloxy- 3-methyl-2-(2-propenyl)cyclopent- 2-ene-1-one (6.27 g) in dichloromethane (30 ml) was added at 0°5° C. in about 10 min. After the mixture was allowed to react for 12 hours at the same temperature, the reaction mixture was diluted with pentane (150 ml), and then a slurry consisting of sodium bicarbonate (150 g) and water (80 ml) was slowly added. After stirring for 2 hours at the same temperature, the reaction mixture was filtered by passing through a celite pad, and the separated layer was dried over anhydrous sodium sulfate. The solvent was evaporated under reduced pressure. The resultant residue was subjected to silica gel column chromatography (eluent; n-hexane: ethyl acetate=50:1) to afford the desired product, (RS)-2-methyl-4-methylidene-3-(2-propenyl)-1-tert-butyldimethylsilyloxycyclopent-2-ene (5.5 g, yield 88.4%) as a pale yellow oil.

$^1$H-NMR (solvent: CDCl$_3$, internal standard: TMS) δ value (ppm): 5.77(m, 1H), 5.0(m, 2H), 4.75(s, 1H), 4.66(s, 1H), 4.65(m, 1H), 2.94(d, 2H), 2.86(dd, 1H), 2.35(brd, 1H), 1.76(s, 3H), 0.91(s, 9H), 0.09(s, 3H), 0.10(s,3H).

③ To a solution of (RS)-2-methyl-4-methylidene- 3-(2-propenyl)-1-tert-butyldimethyl-silyloxycyclopent- 2-ene (1.0 g, obtained above) in dry tetrahydrofuran (10 ml) was added a tetrahydrofuran solution (5.7 ml) of 1M tetrabutylammonium fluoride under ice-water cooling. The solution was then stirred at room temperature for 12 hours. The reaction solution was poured into ice-water, and extracted with ether (100 ml×2). The ether layers were combined and washed with brine, and dried over anhydrous sodium sulfate, and the solvent was evaporated under reduced pressure. The resultant residue was subjected to silica gel column chromatography (eluent; n-hexane: ethyl acetate=3:1) to afford the desired product (RS)-2-methyl-4-methylidene3-(2-propenyl)cyclopent-2-ene-1-ol (460 mg, yield 82.3%) as a pale yellow oil.

$^1$H-NMR (solvent: CDCl$_3$, internal standard: TMS) δ value (ppm): 5.75(m, 1H), 4.90–5.10(m, 2H), 4.82(s, 1H), 4.72(s, 1H), 4.60(brd, 1H), 2.95(m, 3H), 2.35(dd, 1H), 1.89(s, 3H), 1.55(br, 1H).

EXAMPLE 3

① To a solution of (S)-4-hydroxy-3-methyl-2(2-propynyl)cyclopent-2-ene-1-one (20.0 g) in dichloromethane (200 ml) were added with stirring 3,4-dihydro- 2H-pyran (12.5 g) and a catalytic amount of p-toluenesulfonic acid hydrate under ice-water cooling, then the solution was stirred at room temperature for 1.5 hours. This solution was partitioned between diethyl ether and brine, and the organic layer was washed twice with brine. The organic layer was dried over anhydrous sodium sulfate, and then the solvent was evaporated under reduced pressure. The resultant residue was subjected to silica gel column chromatography (eluent; n-hexane:ethyl acetate=5:1) to afford (S)-4-(2-tetrahydropyranyloxy)-3-methyl-2-(2-propynyl)cyclopent- 2-ene-1-one (27 g, yield 86.6%) pale yellow oil.

$^1$H-NMR (solvent: CDCl$_3$, internal standard: TMS) δ value (ppm): 4.79~4.88(m, 1H), 4.70~4.75(m, 0.5H), 4.52~4.61(m, 0.5H), 3.81~4.02(m, 2H), 3.51~3.66(m, 2H), 3.02~3.22(m, 2H), 2.81(dd, 0.5H), 3.02~3.22(m, 2H), 2.50(dd, 0.5H), 2.71(dd, 0.5H), 2.28(dd, 0.5H), 2.31(s, 1.5H), 1.97(brs, 1H), 2.21(s, 1.5H), 1.51~1.93 (m, 4H).

② To a mixture of dibromomethane (26.08 g), zinc dust (29.42 g) and tetrahydrofuran (240 ml) under an atmosphere of argon was added with stirring a dichloromethane solution (100 ml) of 1M titanium tetrachloride under ice-water cooling, then the resulting mixture was stirred for 3 days at 4° C. After dichloromethane (80 ml) was added, a solution of (S)-4(2-tetrahydropyranyloxy)-3-methyl-2-(2-propynyl)-cyclopent- 2-ene-1-one (23.2 g, obtained above) in dichloromethane (100 ml) was added under ice-water cooling. After the addition, the resulting mixture was stirred for 2 hours at the same temperature. Then dibutylhydroxytoluene (antioxidizer, 0.01 g) and hexane (200 ml) were added, and a slurry consisting of sodium bicarbonate (150 g) and water (100 ml) were added, and stirred for 10 min. To a reaction solution separated by decantation was again added a slurry consisting of sodium bicarbonate (70 g) and water (50 ml), and stirred for 2 hours. The reaction solution was filtered by passing through a celite pad, and filtered solution was washed with saturated aqueous sodium bicarbonate solution and brine in sequence, and dried over magnesium sulfate. Then the solvent was evaporated under reduced pressure, and the resultant residue was subjected to silica gel column chromatography (eluent; n-hexane: ethyl acetate=50:1) to afford the desired product, (S)2-methyl-4-methylidene-3-(2-propynyl)-1-(2-tetrahydro-pyranyloxy)- 2-cyclopentene (14.1 g, yield 60.8&) as a pale yellow oil.

$n_D^{24}$1.5180

$^1$H-NMR (solvent: CDCl$_3$, internal standard: TMS) δ value (ppm): 4.70~5.00(m, 3.5H), 4.50(br, 0.5H), 3.91(m, 2H), 3.53(m, 2H), 3.10(m, 2H), 2.30~3.05(m, 2H) 1.96(m, 2.5H), 1.87(s, 1.5H), 1.45~1.85(m, 4H).

EXAMPLE 4

① To a solution of (S)-4-hydroxy-3-methyl-2(2-propynyl)-cyclopent-2-ene-1-one (12.88 g) and triethylamine (13.2 g) in tetrahydrofuran (200ml) was added dropwise chlorotrimethylsilane (10.4 g) for 5 minutes under ice-water cooling, then the solution was stirred for 2 hours under ice-water cooling, and 13 hours at room temperature. Then this solution was poured into ice-water and extracted twice with diethyl ether. The ether layers were combined and washed twice with brine. The separated organic layer was dried over anhydrous magnesium sulfate, and the solvent was evaporated under reduced pressure. The resultant residue was subjected to column chromatography over florisil (eluent; n-hexane:ethyl acetate=20:1) to afford (S)-4-trimethylsilyloxy-3-methyl-2-(2-propynyl )-cyclopent- 2-ene-1-one (18.0 g, yield 79.1% ) as a pale yellow oil.

$^1$H-NMR ( solvent: CDCl$_3$, internal standard: TMS) δ value (ppm): 4.66(brd, 1H), 3.12(m, 2H), 2.73(dd, 1H), 2.25(dd, 1H), 2.15(s, 3H), 1.95(t, 1H), 0.19(s, 9H).

② Under an atmosphere of argon, zinc dust (23.5 g) and dibromomethane (21 g) were added to tetrahydrofuran (190 ml), and a dichloromethane solution (80 ml) of 1M titanium tetrachloride was added thereto under ice-water cooling. After the addition, stirring was continued at 4° C. for 3 days. A solution of (S)-4-trimethylsilyloxy- 3-methyl-2-(2-propynyl) cyclopent-2-one-1-one (17.8 g) in dichloromethane (80 ml) was added to said reaction solution under ice-water cooling. After the addition, the resulting mixture was allowed to react for 2 hours at the same temperature. After the addition of hexane (240 ml), a slurry consisting of sodium bicarbonate (120 g) and water (64 ml) was added thereto under ice-water cooling. About 10 min. thereafter, the reaction solution was separated by decantation, then a slurry consisting of sodium bicarbonate (120 g) and water (64 ml) was added thereto under ice-water cooling, and stirred for 2 hours. The reaction solution was filtered by passing through a celite pad, and filtered solution was washed with saturated aqueous sodium bicarbonate solution and brine, and dried over sodium sulfate. Then the solvent was evaporated under reduced pressure. The resultant residue was subjected to silica gel column chromatography (eluent; n-hexane: ethyl acetate=3:1) to afford the desired product: (S)-2-methyl-4-methylidene-3-(2-propynyl)- 1-trimethylsilyloxy-2-cyclopentene (5.22 yield 29.6%) and (S)-2-methyl-4-methylidene-3-(2-propynyl)cyclopent- 2-ene-1-ol (3.5 g, which correspond to a yield of 46.1%) as a deprotected product.

(S)-2-methyl-4-methylidene-3-(2-propynyl)-1-trimethylsilyloxy- 2-cyclopentene $[\alpha]_D^{23}$–68.3° (c=2.02, CHCl$_3$)

$^1$H-NMR (solvent: CDCl$_3$, internal standard: TMS) δ value (ppm): 4.92(s, 1H), 4.78(s, 1H), 4.63(br, 1H), 3.08(m, 2H), 2.89(m, 1H), 2.36(m, 1H), 1.93(t, 1H), 1.83(s, 3H), 0.15(s, 9H).

(S)-2-methyl-4-methylidene-3-(2-propynyl)-cyclopent-2-ene-1-ol mp. 73.2° C.

$[\alpha]_D^{23}$–116.1° (c=2.43, CHCl$_3$)

$^1$H-NMR (solvent: CDCl$_3$, internal standard: TMS) δ value (ppm): 4.98(s, 1H), 4.85(s, 1H), 4.62(br, 1H), 3.10(d, 2H), 3.00(m, 1H), 2.39(m, 1H), 1.96(t, 1H), 1.92(s, 3H), 1.55(br, 1H).

Production of (RS)-2-methyl-4-methylidene-3(2-propenyl)cyclopent-2-ene-1-ol from (RS)-3-methyl-2(2-propenyl)-4-hydroxycyclopent-2-ene-1-one by Wittig reaction Ether (125 ml), t-butanol (13.2 ml) and methyltriphenylphosphonium bromide (50 g) were mixed with stirring at room temperature, then potassium t-butoxide (25.7 g) was added portionwise to the mixture and then the resulting solution was stirred for 5 hours at the same temperature. To the solution was added a solution of (RS)-3-methyl-2-(2-propenyl)-4-hydroxy-cyclopent- 2-ene-1-one (26.0 g) in ether (25 ml) under ice-water cooling and the resulting reaction mixture was stirred at the same temperature for 2 hours and then for 6 hours at room temperature. The reaction solution was poured into a saturated aqueous solution of sodium dihydrogenphosphate, and the product was extracted with ether. The obtained ether layer was washed with brine and dried over anhydrous magnesium sulfate. Then the filtered solution was evaporated. The obtained oily residue was then subjected to silica gel column chromatography to afford (RS)-2-methyl-4-methylidene3-(2-propenyl)cyclopent-2-ene-1-ol (10.0 g) in a yield of 40%.

Production of (S)-2-methyl-4-methylidene-3-(2-propynyl)cyclopent- 2-ene-1-ol from (S)-3-methyl-2-(2-propynyl)- 4-hydroxycyclopent-2-ene-1-one by Wittig reaction Ether (70 ml), t-butanol (6.6 ml) and methyltriphenylphosphonium bromide (25 g) were mixed with stirring at room temperature, then potassium t-butoxide (12.9 g) was added to the mixture and then the resulting solution was stirred for 5 hours at the same temperature. To the solution was added a solution of (S)-3-methyl-2-(2-propynyl)-4-hydroxycyclopent-2-ene-1one (12.42 g) in ether (13 ml) under ice-water cooling and the resulting reaction mixture was stirred at the same temperature for 2 hours and then for 6 hours at room temperature. The reaction solution was poured into a saturated aqueous solution of sodium dihydrogenphosphate, and extracted with ether. The obtained ether layer was washed with brine and dried over anhydrous magnesium sulfate. Then the filtered solution was evaporated. The obtained oily residue was then subjected to silica gel column chromatography, however, neither the desired product, (S)-2-methyl-4-methylidene-3-(2-propynyl)cyclopent-2-ene-1-ol nor the starting material was obtained.

Production of (S)-2-methyl-4-methylidene-3-(2-propynyl)cyclopent- 2-ene-1-ol by a reaction of (S)-4-hydroxy-3-methyl-2-(2-propynyl)cyclopent-2-ene-1-one and dibromomethane, zinc and titanium tetrachloride Dibromomethane (1.3 g) and zinc dust (1.5 g) were added to dry tetrahydrofuran (20ml), and the resulting mixture was cooled to 0°~5° C. A dichloromethane solution (5 ml) of 1M titanium tetrachloride was added to the tetrahydrofuran solution over about 10 min, and the resulting mixture was allowed to react for 3 days at 0°5° C. Then a solution of (S)-4-hydroxy-3-methyl-2-(2-propynyl)cyclopent- 2-ene-1-one (675 mg) in dichloromethane (10 ml) was added at 0°~5° C. over about 10 min. After the resulting mixture was allowed to react for 2 hours at the same temperature, hexane (40 ml) and then a slurry consisting of sodium bicarbonate (8 g) and water (4 ml) were added. After stirring for 2 hours at 0°~5° C., the organic layer was separated by decantation. The obtained residue was extracted three times with n-hexane (20 ml). The combined organic layer was washed with saturated aqueous sodium bicarbonate solution, and dried over anhydrous magnesium sulfate. Then the solvent was evaporated under reduced pressure, and the resultant residue was subjected to silica gel column chromatography (eluent; n-hexane: ethyl acetate=3:1) to afford the desired product, (S)-2-methyl-4-methylidene-3-(2-propynyl)cyclopent-2-ene-1-ol (17 mg, yield 2.6% as a pale yellow oil.

What is claimed is:

1. A process for the production of a cyclopentenol compound represented by the formula I:

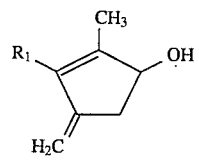

wherein $R_1$ represents a 2-propenyl group or a 2-propynyl group, which comprises the steps of;

(i) protecting the hydroxyl group of the cyclopentenolone compound II:

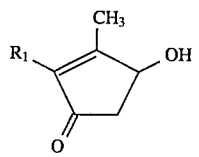

wherein $R_1$ is the same as defined above to give a cyclopentenolone derivative represented by the formula III:

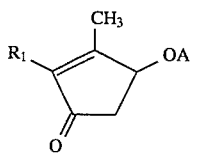

wherein $R_1$ is the same as defined above and A is a protecting group for the hydroxyl group;

(ii) reacting a mixture of zinc and dibromomethane or diiodomethane in an inert organic solvent with titanium tetrachloride;

(iii) reacting the resulting reaction mixture with a cyclopentenolone derivative III to give a cyclopentenol derivative IV:

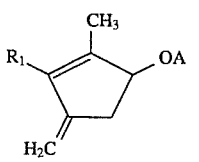

wherein $R_1$ and A are the same as defined above; and (iv) removing the protecting group A from the cyclopentenol derivative represented by the formula IV to give the cyclopentenol compound I.

2. A process for the production of a cyclopentenol derivative represented by the formula IV:

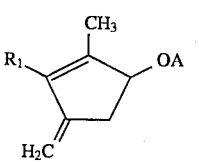

wherein $R_1$ represents a 2-propenyl group or a 2-propynyl group; and A represents a protecting group for a hydroxyl group, which comprises the steps of;

(i) reacting a mixture of zinc and dibromomethane or diiodomethane in an inert organic solvent with titanium tetrachloride; and (ii) reacting the resulting reaction mixture with a cyclopentenolone derivative represented by the formula III:

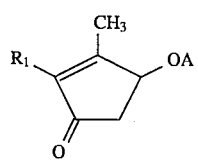

wherein $R_1$ and A are the same as defined above.

3. A process according to claim 1, wherein the protecting of the hydroxyl group of the cyclopentenolone compound II is carried out by reacting the cyclopentenolone compound II with a tri($C_1$–$C_6$)alkylsilylchloride or a tri($C_1$–$C_6$)alkylsilyltriflate in the presence of an organic base, and the removing of the protecting group A from the cyclopentenol derivative IV is carried out by reacting the cyclopentenol derivative IV with a fluoride ion or an acid.

4. A process according to claim 1, wherein the protecting of the hydroxyl group of the cyclopentenolone compound II is carried out by reacting the cyclopentenolone compound II with a ($C_1$–$C_2$)alkyl chloride substituted with a ($C_1$–$C_2$)alkoxy group at the α-position in the presence of an organic base, and the removing of the protecting group A from the cyclopentenol derivative IV is carried out by reacting the cyclopentenol derivative IV with an acid.

5. A process according to claim 1, wherein the protecting of the hydroxyl group of the cyclopentenolone compound II is carried out by reacting the cyclopentenolone compound II with a dihydrofuran or a dihydropyran in the presence of an acid, and the removing of the protecting group A from the cyclopentenol derivative IV is carried out by reacting the cyclopentenol derivative IV with an acid.

6. A cyclopentenol derivative represented by the formula IV:

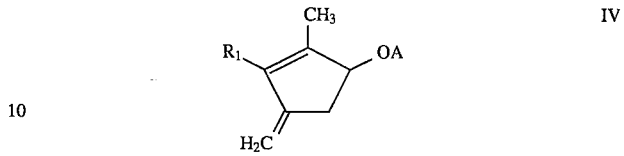

wherein $R_1$ represents a 2-propenyl group or a 2-propynyl group; and A represents a protecting group for a hydroxyl group.

7. A cyclopentenol derivative according to claim 6, wherein $R_1$ represents a 2-propenyl group or a 2-propynyl group; and A represents a tri($C_1$–$C_6$)alkylsilyl group, a 2-tetrahydrofuranyl group, a 2-tetrahydropyranyl group or a ($C_1$–$C_2$)alkyl group substituted with a ($C_1$–$C_2$)alkoxy group at the α-position.

8. The process of claim 1 wherein $R_1$ represents a 2-propynyl group.

9. The process of claim 2 wherein $R_1$ represents a 2-propynyl group.

10. The cyclopentenol derivative of claim 6 wherein $R_1$ represents a 2-propynyl group.

* * * * *